United States Patent [19]
Cuilleron et al.

[11] Patent Number: 5,397,347
[45] Date of Patent: Mar. 14, 1995

[54] ARTIFICIAL HEART VALVE

[75] Inventors: Jean Cuilleron, Saint Etienne; Eugene M. Baudet, Merignac, both of France

[73] Assignee: Fabrique D'Implants et D'Instruments Chirurgicaux Sarl, France

[21] Appl. No.: 57,211

[22] Filed: May 3, 1993

Related U.S. Application Data

[63] Continuation of Ser. No. 718,605, Jun. 21, 1991, abandoned.

[30] Foreign Application Priority Data

Jun. 22, 1990 [FR] France .................. 90 08191

[51] Int. Cl.⁶ .................................... A61F 2/24
[52] U.S. Cl. ................................ 623/2; 137/527
[58] Field of Search ................. 623/2; 137/512.1, 527

[56] References Cited

U.S. PATENT DOCUMENTS

| | | | |
|---|---|---|---|
| 3,546,711 | 12/1970 | Bokros | 623/2 |
| 4,178,639 | 12/1979 | Bokros | 623/2 |
| 4,443,894 | 4/1984 | Klawitter | 623/2 |
| 4,863,458 | 9/1989 | Bokros | 623/2 |
| 4,892,540 | 1/1990 | Vallana | 623/2 |

*Primary Examiner*—Randall L. Green
*Assistant Examiner*—Mary Beth O. Jones
*Attorney, Agent, or Firm*—Eckert Seamans Cherin & Mellott

[57] ABSTRACT

An artificial heart valve is the combination of curved wings and a ring inside of which the curved wings are hinged. The ring extends between an inlet and an outlet end, which ends are bisected by a center plane. The ring has diametrically opposed shoulders on the inlet end, and each shoulder is formed with a pair of hemispherical cavities. Each curved wing has a pair of opposite hemispherical enlargements shaped to cooperate with the hemispherical cavities in the shoulders such that spaced pivot axes are defined for the curved wings. The hemispherical enlargements are arranged on the wings and the hemispherical cavities are correspondingly arranged on the ring such that the curved wings, when in an extreme open position of approximately at least 85 degrees to the center plane of the ring, project minimally beyond the outlet end of the ring. Preferably, any length of the curved wings that would project beyond the outlet end would be less than an axial length of the ring. The curved wings, when in the open position, delimit three equivalent flow areas to promote a central axial and laminar flow. The hemispherical enlargements are integrated into a thickness of the ring so that there is a smooth surface in the regions of the hemispherical enlargements and cavities. The smooth surface avoids disturbing or interfering with the central laminar flow. Preferably, the curved wings and the ring are formed from titanium and covered with a film of amorphous and isotropic carbon.

5 Claims, 3 Drawing Sheets

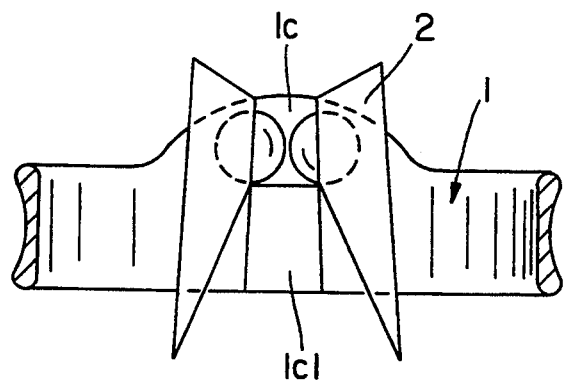
FIG. 3
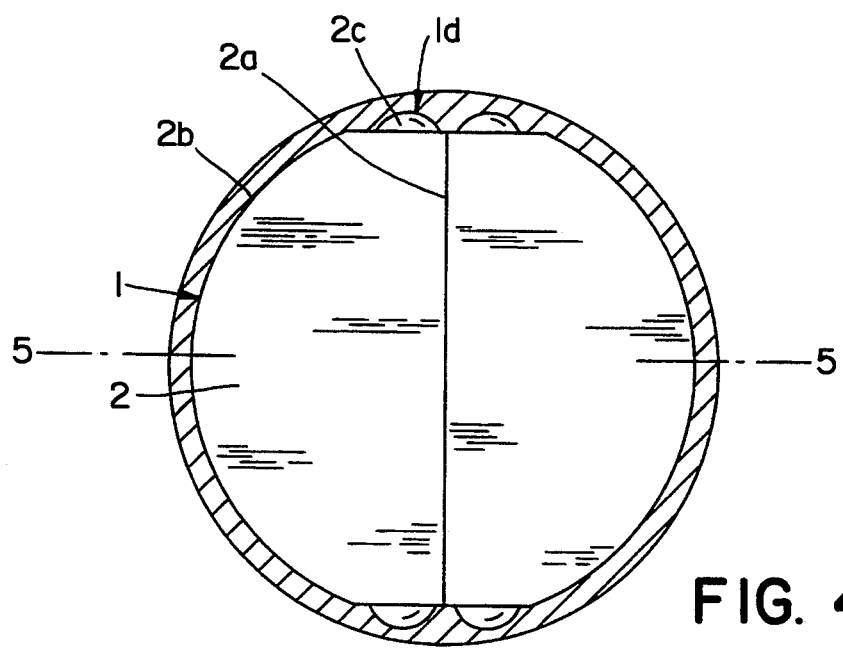
FIG. 4
FIG. 5
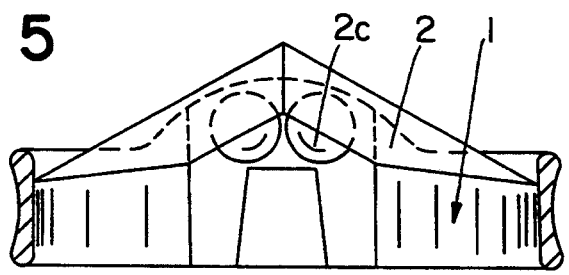

ARTIFICIAL HEART VALVE

This is a continuation division of application Ser. No. 07/718,605, filed Jun. 21, 1991, now abandoned.

BACKGROUND OF THE INVENTION

For certain valvular lesions due to various causes, it is sometimes necessary to implant artificial heart valves, the mechanical structure of which allows for a mitral or aortic valvular unit to be replaced.

Considering the functions an artificial heart valve must fulfill, insofar as possible, it is important the latter meets several criteria:

The valve must ensure its function for a period beyond the life expectancy of the patient regardless of his/her age at the time when the valve was implanted, Therefore, the characteristics of the valve must be determined accordingly.

The valve must provide a central laminar flow without upstream or downstream turbulences in order to meet hemodynamic performances so as not to create significant transvalvular gradients through the implant, This is particularly the case for valves with a small diameter.

Considering the presence of stasis areas resulting from the principle of the mechanism of the artificial valves, fibrocruoric clots may form at the level of this mechanism thereby being likely to break away from and migrate into the systemic circulation. Besides, thrombosis responsible for blockage of the valve mechanism may result from this.

In order to reduce this phenomenon of thrombogenicity, an anticoagulant treatment administered by oral route is usually called for, This treatment is aimed at limiting the formation of clots at the valve mechanism.

To date, several types of valves have been offered with different technological designs, determined in an attempt to achieve the aforementioned aims as much as possible.

For example, valves, the mechanism of which mainly includes a ball freely moving in a metal cage with bows integral to a metal ring, are known. A ball in the blood flow, can be responsible for a mainly lateral flow, meaning the hemodynamic performances are not satisfactory.

In order to improve these hemodynamic performances, a valve with a rocking disk creating a lateral flow and a main area and secondary area, was offered. However, it was noticed that this secondary area is responsible for stasis, consequently leading to thrombosis phenomena even in the case of anticoagulant treatment.

In an attempt to overcome these disadvantages and solve the problems relating to the hemodynamics and thrombogenicity, artificial heart valves with two wings hinged inside a ring, are proposed. The valve known under the name of the "ST JUDE MEDICAL" valve can be quoted as an example, with two flat wings fitted with hinges in the ring of the prosthesis and allowing opening of the said wings at an angle in the region of 85 degrees. Consequently a virtually central and laminar flow results. Furthermore, with this type of valve, the plane of the wings in the open position, exceeds the plane of the ring very slighty, thus avoiding, (particularly in the mitral position), interfering with the opening and closing movement of the wings by sub-jacent anatomical structures.

However, it appears that when the wings are in the open position, the valve does not have three equivalent areas. The two lateral areas each represent virtually 40 percent, whereas the central area only represents 20 percent. Therefore, it appears that the central area is less used than the lateral areas so that stasis phenomena at this level with insufficient blood flushing, can generate a phenomenon of thrombosis requiring anti-coagulant treatment.

Other types of valves with curved wings are also known. As opposed to those described above, these have three equivalent areas when the wings are in the open position. Clinical tests have shown that the adoption of three equivalent areas, significant limits valvular thrombosis phenomena. On the other hand, if one could consider that the problem of thrombogenicity was overcome, the same cannot be applied to the problem of hemodynamics. In fact, the opening of the wings is limited to approximately 76 degrees, creating oblique flow due to this in the lateral areas. Another disadvantage also appears concerning the technological design in that when the valve is in the open position, the wings are well outside the ring which can lead to blocking incidents of the said wings by sub-jacent ventricular structures, particularly in the mitral position.

This state of the art can be illustrated by the teaching of the Patent EP 0338179. Besides the fact that when the wings are in the open position, they are well outside the plane of the ring, other disadvantages and problems arise considering the structure of the valve.

A first disadvantage arises at the hinge of the wings in the ring which does not limit (between the ends of the wings) a totally smooth surface but profiled recesses likely to interfere with the central laminar flow.

Another disadvantage also appears on closure of the wings which are applied against the ring, which gives rise to a repetitive noise for the patient and those around him/her.

Finally, it is highlighted, considering the type of material making up the wings, the latter are relatively thick meaning they do not have enough elasticity to absorb the kinetic energy stored by the speed of the blood flow.

SUMMARY OF THE INVENTION

The invention is aimed at overcoming these disadvantages and the problem brought up, i.e. to design an artificial heart valve, the characteristics of which are determined to solve both the problem of the hemodynamics and thrombogenicity as well as the significant problem of the noise on closure of the wings.

In order to achieve these aims, in an overall manner, a heart valve was designed of the type comprising a ring, the inside of which has curved hinged wings and is remarkable due to the combination of the following elements:

a) diametrically opposed fittings likely to offset the hinging means of the wings so that when in the maximum opening position of approximately at least 85°, the latter only project very slightly into the plane of the ring thereby limiting (in combination with the profile of the wings) three equivalent areas providing a central axial and laminar flow;

b) the hinging means are built into the thickness of the ring so that the ends of the wings are separated at the level of the fittings, thereby limiting a totally free space so as not to limit or interfere with the central flow;

c) the wings are made of titanium or titanium alloy covered with a film of amorphous and isotropic carbon or titanium nitride.

Considering the type of materials of the wings in particular, it is possible to make them very thin and provide them with controlled elasticity. Consequently, at the time of closure of the wings, the kinetic energy stored by the speed of the blood flow is absorbed by the wings creating an instantaneous pressure upstream and partial vacuum downstream. The higher the elasticity of the assembly, the lower the pressure and vacuum.

It also appears that the deformation of the wings associated to the rubbing against the body at the end, form a damper on closure, enabling the deceleration time of the moving assembly to be extended. Consequently, the blood flow surge pressure phenomenon is sharply reduced which results in lowering the closing noise of the wings and increasing the braking time thereby eliminating all cavitation phenomena downstream to the wings.

Therefore, it is noticed that the valve, according to the invention, has minimum thrombogenicity, providing, if required, in post-operative periods, a low anticoagulation rate due to the reduction in the stasis areas, considering the reduction in the transprosthetic gradient, the presence of an axial and laminar flow also distributed at the three equivalent areas, and flushing the two sides of the wings thoroughly.

As indicated, the opening angle of each wing is in the region of at least 85 degrees.

In an advantageous manner, the ring has two projecting parts making up two lugs or bosses projecting from the ring in order to take the hinges of the wings still positioned the admission end in mitral or aortic position.

In order to have an opening position of the wings at 85 degrees, by limiting three equivalent areas, the flat parts of the ring have projecting means providing locking of the wings in an open position, according to an angle of at least 85 degrees, thereby limiting three equivalent areas.

The problem brought up, i.e. to obtain three equivalent areas, is overcome by the curving of the wings.

The wing locking means made up of a projection, project from internal flat surfaces of the ring at the lugs.

In order to overcome the problem brought up, firstly to provide flushing and cleaning of the internal surface of the ring where the wings are hinged, and, secondly, to have a wide enough and totally free surface between the wings at the hinge in order to disturb the central flow, the hinge of these wings is made of hemispherical male parts formed by projecting from the profile of each wing and likely to cooperate with complementary hemispherical cavities formed in the two lugs of the ring.

In a particularly advantageous manner, it is noticed that this design of wing hinge enables a totally free space to be left between the ends of the said wings, free from any hollow or raised asperities, consequently enabling a central flow in optimum conditions.

Furthermore, consequently, the hinges are washed thanks to a slight clearance or reduction in the section of the hemispherical male parts in their complementary cavity due to the alternating bending movement of the wings providing a flow and backflow at this moment, cleaning the said cavities.

The hemispherical male parts can be designed in a three-blade form with three recesses offset by 60 degrees.

In order to close the valve, the ends of the wings, on contact with the ring, have a curved shape, perfectly matching the internal diameter of the ring, the closure between the two other ends is carried out by curvilinear and close-joining contact over the whole curve of the wings in contact.

Still with the aim of obtaining high mechanical and optimum hemodynamic characteristics so as not to slow down the blood flow or enhance the formation of thrombosis, the choice of different materials making up the valve proves to be particularly important. Wings and, if required, the ring, made of titanium or titanium alloy covered with a film of amorphous and isotropic carbon, proves to be particularly suitable to overcome such a problem.

BRIEF DESCRIPTION OF THE DRAWINGS

The invention is described below in more detail by the accompanying drawing in which:

FIG. 3 is a cross section taken along line 3—3 of FIG. 2.

FIG. 4 is a view similar to FIG. 2 with the wings in the closed position.

FIG. 5 is a cross section taken along line 5—5 of FIG. 4.

DETAILED DESCRIPTION OF THE INVENTION

Figures 1, 2:
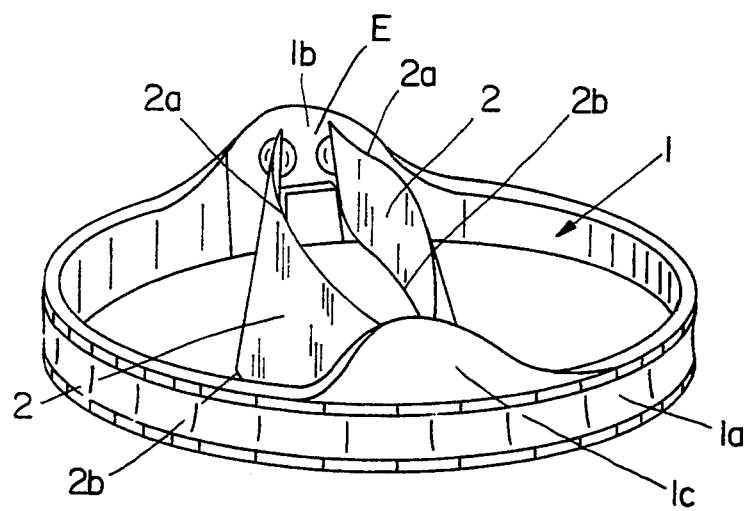
FIG. 1 is a perspective view of the valve with the wings in the open position according to the invention.
FIG. 2 is a large scale front view of a partial section of the valve with the wings in the open position.
Figure 6:
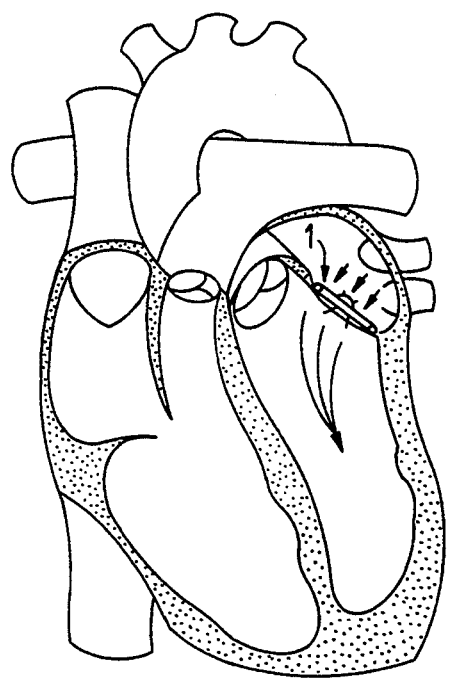
FIG. 6 shows the implantation of the valve in a mitral position.
Figure 7:
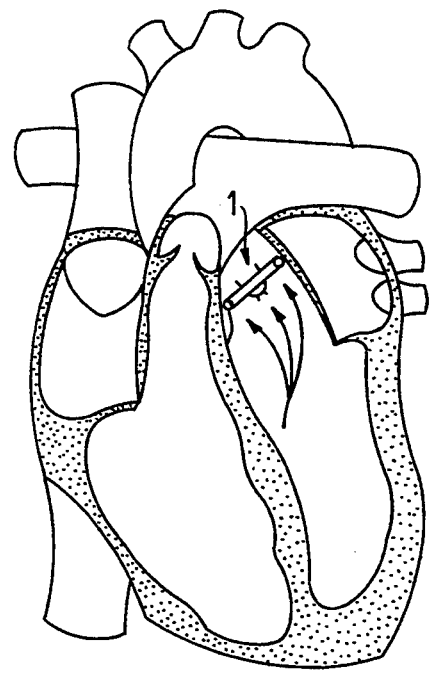
FIG. 7 shows the implantation of the valve in an aortic position.
Figure 8:
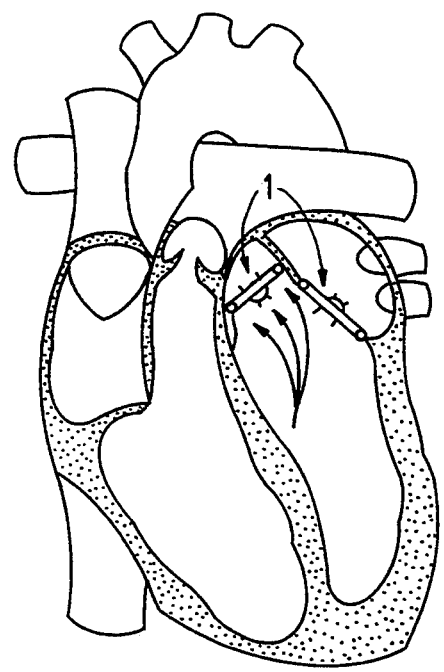
FIG. 8 shows the implantation of the valve in a double, mitral and aortic position.

As shown in FIG. 1, the artificial valve comprises a ring (1) inside of which two identical wings (2) are hinged. The ring (1) has any external fitting enabling, in a known manner, a fabric collar to be inserted in order to make up the suture ring as such. For example, these fittings are made up of a groove (1a).

It is reminded that the valve is destined to both replace the mitral valve and the aortic valve without any modification other than the suture ring, whose shape differs according to the position anticipated: aortic or mitral.

According to the invention, the ring (1) has internal fittings likely to provide the hinge for the wings (2) according to a maximum opening position in order to limit, in combination with the profile of the wings, three equivalent areas (A1, A2, A3) providing a central, axial and laminar flow. Furthermore, according to another characteristic, and as shall be indicated in the following description, the internal fittings of the ring, enable them to be integrated inside the ring when the wings (2) are closed.

As shown in FIGS. 1, 3 and 5 in particular, the internal fittings of the ring (1), are made up of two diametrically opposed parts (1b and 1c), formed directly by projecting from one of the faces of the ring thereby making up shoulders or lugs. Each of the parts (1b, 1c) appear on valve intake face end. The two projecting parts (1b, 1c)

taking-the hinge mechanism of the wings (2) and making up shoulders or lugs, offset the mechanism so that in the opening position, the wings (2) only project from the plane of the ring very slightly, this varying according to their size.

The valve is essentially ring shaped, as shown in FIGS. 1 and 3. The valve controls blood flow from upstream to downstream through a heart pathway in the manner of a checkvalve, having an inlet end (the top in FIGS. 1 and 3) and an outlet end (the bottom), along which flow is permitted in one direction only. The valve occupies a length along the pathway between the inlet end and the outlet end, the ring defining a center plane between the inlet end and the outlet end disposed transverse to the direction of flow. As seen in FIG. 3, where the valve is shown open, the length of the wings projecting downstream from the outlet end is very slight, less than the length of the ring along the pathway.

According to another characteristic, each of parts (1b, 1c) makes up, over the whole width of the ring, an internal flat surface with projecting means (1b1, 1c1) designed to angularly lock the wings according to an angle of at least 85 degrees. With this aim in mind, these means (1b1, 1c1), are each made up of a boss formed by projecting from the internal flat surface face of each parts (1b1, 1c1), opposite the shoulder taking the hinge mechanism of the wings. The side edges of each boss (1b1, 1c1) are sloped according to a suitable angle to enable, as indicated, the locking of each of the wings in an open position, at least 85 degrees. Furthermore, this angle is determined so that then the wings are in the open position, the latter tend to converge in the direction of each of the shoulders (1b, 1c) taking the hinge mechanism (figure According to another characteristic, each of the wings has a profile with a curved section so that when in the open position, the central opening limited by the wings, has a central area (A2) equivalent to or greater than each of the two lateral areas (A1 and A3). This open position, limited to at least 85 degrees, enables and axial and laminar flow to be provided.

The opposite edges (2b) of each of wing (2) are profiled according to a curve likely to match the internal radius of the ring. Edges (2a) have a suitable curve, determined to provide close-joining contact between the two wings. When in the closed position, the wings form an obtuse angle.

The hinge of each of the wings (2), at the flat surface of the shoulders (1b, 1c), is made of hemispherical male parts (2c) formed at each end directly in the extension of the edges of each wing. Each of these hemispherical parts (2c) is likely to cooperate with complementary hemispherical cavities (1d) formed at the flat surface of each shoulder. These cavities (1d), are only a few millimeters apart. It is to be noted that the hemispherical male part integral to the wing, can be made up of either a full hemisphere or a three-blade hemisphere in which three recesses are cut, angularly offset according to an angle of approximately 60 degrees. Such arrangements enable each of the hinge movements to provide flushing of the concave surface aimed at limiting the formation of thrombosis at the hinge.

In a particularly important manner and as shown in FIGS. 1, 2 and 4 of the drawings, the integration of hinge parts (2c) into the complementary cavities (1d), allow a big enough space (E) between the ends of the wings. This free space (E) does not have any hollow or raised asperity likely to represent an obstacle for the central laminar flow.

Regardless of the embodiment, considering the principle of the mechanism defined above, this latter offers no point of stasis for the blood flow. The only structures fixed in this field of action of the valve result from the thickness of the wings which can be extremely reduced according to the type of material used.

According to another important characteristic of the invention, the ring (1) and wings (2) are made of titanium or titanium alloy covered with a film of amorphous and isotropic carbon. The high strength of this titanium alloy allows for very thin wings and ring thereby considerably increasing the mechanical characteristics of the valve. Furthermore, the film covering the titanium in the form of a thin coat of amorphous carbon, makes up a continuous structure of a completely smooth, non porous aspect with less surface tension. Consequently, there is very low wettability, providing a flow of blood without deceleration and very good hemodynamic performances.

The advantages are made well apparent from the description. The following is to be highlighted and reminded in particular:

The useful geometrical opening greater than that of pyrolytic carbon valves, with an equivalent outside diameter, considering, firstly, the thin ring which enables a greater cross section of passage and, secondly, the thin wings and the said ring made of titanium or titanium alloy.

The opening of the wings according to an angle of at least 85 degrees forming three equivalent areas authorizing a central, axial and laminar flow.

The integration of the hinge mechanism into the ring consequently reduces fixed structures responsible for stasis areas.

The low profile of the valve enables the wings to be free from interference with sub-jacent anatomical elements as the wings in the open position project from the plane of the ring by virtually nothing at all.

The application of the titanium-amorphous carbon substrate material allows for very thin mobile parts, reducing weight, therefore inertia, enabling the cross section of the passage of blood flow to be increased substantially which should reduce the losses of transvalvular loads.

The deformation of the wings, considering the type of materials they are made up of, acts as a damper on closure, enabling, firstly, the deceleration time to the extended and, secondly, the closing noise to be reduced.

The large, totally free space which appears between the ends of the wings at the hinge.

We claim:

1. Artificial heart valve which is surgically implanted in a heart pathway for controlling blood flow from upstream to downstream through the pathway, the artificial heart valve comprising:

a ring having an inlet end, an outlet end, and a length extending along the pathway between the inlet end and the outlet end, the ring defining a center plane positioned and oriented generally midway between the inlet end and the outlet end;

a pair of curved wings hingedly attached within the ring, each of the curved wings being movable about a pivot axis from a closed position whereby the blood flow through the pathway is blocked, to an open position whereby the blood flow is enabled, the curved wings defining an angle of at least 85 degrees to the center plane of the ring when in the open position; and, each curved wing extending between a first edge and a spaced second edge, and between spaced hinging means positioned between the first and second edges in respectively opposite positions;

each first edge being shaped in a curve and arranged to match and engage in close-joining contact an internal radius of the ring;

each second edge being shaped in a curve and arranged to match and engage in close-joining contact the second edge of the other wing;

each curved wing being shaped and arranged to define, between the spaced hinging means, a curved section-profile; and, each hinging means comprising a male hemispherical part;

wherein the ring defines a pair of diametrically opposed parts projecting upstream from the center plane at the inlet end, the diametrically opposed parts defining hemispherical cavities for accepting and cooperating with the hemispherical parts of the curved wings to exclusively limit the relative movement between the wings and the ring to pivotal movement;

the hemispherical cavities defining the pivot axis for each of the curved wings, the pivot axes being disposed upstream from the center plane of the ring;

the hemispherical parts being arranged on the curved wings and the hemispherical cavities being cooperatively arranged in the opposed parts such that, when the curved wings are in the open position, a length of the curved wings projecting downstream from the outlet end is less than the length of the ring;

the hemispherical cavities being integrated into a thickness of the ring such that attached ends of one curved wing, which attached ends are attached to the hemispherical parts and are positioned between the spaced first and second edges are separated from the corresponding attached ends of the other curved wing by a distance, and additionally such that depressed, and raised, asperities in the thickness of the ring are generally excluded, which together with said distance cooperatively avoids detracting from a central laminar flow of blood in the valve;

the curved wings and ring cooperatively defining in the center plane three flow areas when the curved wings are in the open position, wherein the flow areas are substantially equivalent in area.

2. Artificial heart valve according to claim 1, wherein at least one of the curved wings and the ring comprise titanium and is covered with a film of amorphous and isotropic carbon.

3. Artificial heart valve according to claim 1, wherein the diametrically opposed parts are integral extensions of the inlet end.

4. Artificial heart valve according to claim 3, further comprising means for locking the curved wings in the open position.

5. Artificial heart valve according to claim 4, wherein the means for locking includes a boss projecting from an internal face of the ring.

* * * * *